United States Patent [19]

Harris et al.

[11] Patent Number: 4,673,879
[45] Date of Patent: Jun. 16, 1987

[54] EDDY CURRENT FLAW DETECTOR HAVING ROTATABLE FIELD DEFINING SLEEVE FOR SELECTIVELY ENHANCING INDUCED EDDY CURRENTS IN A WORKPIECE

[75] Inventors: Richard M. Harris, North Royalton; David A. Valek, Parma; James M. Toth, Lyndhurst; Richard F. Abramczyk, Brunswick, all of Ohio

[73] Assignee: Rupublic Steel Corporation, Cleveland, Ohio

[21] Appl. No.: 625,029

[22] Filed: Jun. 27, 1984

[51] Int. Cl.$^4$ .................... G01N 27/90; G01N 27/82; G01R 33/12
[52] U.S. Cl. .................... 324/240; 324/238; 324/237; 324/262; 336/84 C
[58] Field of Search ............... 324/225, 227, 228, 233, 324/234–243, 226, 262, 219–221, 209; 336/84 R, 84 C

[56] References Cited

U.S. PATENT DOCUMENTS

| | | | |
|---|---|---|---|
| 2,102,451 | 12/1937 | Zuschlag | 324/241 X |
| 2,938,162 | 5/1960 | Roffman et al. | |
| 2,998,566 | 8/1961 | Cochran | |
| 3,056,081 | 9/1961 | Hochschild | |
| 3,110,860 | 11/1963 | Allen | |
| 3,152,302 | 10/1964 | Allen et al. | |
| 3,419,797 | 12/1968 | Libby | 324/229 X |
| 3,872,379 | 3/1975 | Brooks et al. | 324/242 |
| 4,123,708 | 10/1978 | Vild et al. | 324/240 X |
| 4,203,069 | 5/1980 | Davis | |
| 4,337,431 | 6/1982 | Hale | 324/220 |
| 4,507,610 | 3/1985 | Nakaoka | 324/238 |

FOREIGN PATENT DOCUMENTS

| | | | |
|---|---|---|---|
| 1138962 | 10/1962 | Fed. Rep. of Germany | 324/209 |
| 097486 | 8/1979 | Japan | 324/262 |
| 565248 | 8/1977 | U.S.S.R. | 324/240 |

Primary Examiner—Reinhard J. Eisenzopf
Assistant Examiner—Warren S. Edmonds
Attorney, Agent, or Firm—Watts, Hoffmann, Fisher & Heinke Co.

[57] ABSTRACT

Method and apparatus for scanning a generally cylindrical workpiece for flaws. A cylindrical metallic sleeve is rotatably supported about a workpiece path of travel. Two differentially wound energization coils surround the sleeve near two apertures in the sleeve. The coils are energized with a high frequency signal that induces eddy currents in the workpiece. The apertures periodically disrupt the eddy current inducing magnetic fields and enhances signals from the coils indicative of the presence of flaws in the workpiece.

20 Claims, 10 Drawing Figures

EDDY CURRENT FLAW DETECTOR HAVING ROTATABLE FIELD DEFINING SLEEVE FOR SELECTIVELY ENHANCING INDUCED EDDY CURRENTS IN A WORKPIECE

TECHNICAL FIELD

The present invention relates to an eddy current tester for detecting flaws along the surface of an elongted workpiece such as a steel bar or pipe.

BACKGROUND ART

In the production of steel products it is desirable to detect manufacturing flaws as soon as possible so that remedial steps can be taken to eliminate the cause of those flaws, and to repair a flawed workpiece or reject it before it is further processed. The process steps in manufacturing steel are well documented and will not be described in detail. Briefly, molten iron is treated with oxygen and other agents are added in varying amounts to produce molten steel which is poured into molds to produce ingots or a continuous caster to produce slabs or billets. Each billet in turn is heated and shaped into a bloom, a large block of steel anywhere from 10" to 16" in thickness and 20' to 30' in length. These blooms are stored and reheated when further shaping is desired. To make steel bars, a bloom is first formed into a billet which is a square typically 2" to 6" in cross-section and approximately 30" long.

The billet is heated to a temperature of approximately 2300°-2400° F. so that it becomes pliable enough to be rolled into a bar shape. The rolling process produces an elliptical shape which is gradually rounded as it passes through subsequent rolling stages. After the billet has been rolled it is much longer and narrower. By way of example, a 5" cross-section billet can be rolled into a round steel bar approximately $\frac{5}{8}$" in diameter and hundreds of feet long. The steel bar is then cut into pieces of a desired length for shipment.

Various inspection steps are performed on the billet prior to rolling. These inspection steps in theory detect the existence of flaws in the billet which would produce flaws in the resulting bar product. Once the billet flaws are detected they are removed by scarfing or other procedures. During the rolling of the billet, however, other defects may be introduced. A piece of foreign matter may be stuck to the roll and introduce repetitive elongated scratches or grooves in the steel as rolling occurs. If the rolls become misshaped, they can generate severe irregularities in the steel bar which on subsequent rolling may become folded over to also form elongated grooves or flaws along the bar. If the causes of these defects are not detected as soon as possible, many bars having these defects will be produced.

If the steel bars contain flaws of less than a certain depth, the bars may be sold for their intended purpose. If, however, the flaws exceed a certain depth, the bars are scrapped and must be reprocessed with loss in productivity and at additional expense. It is apparent that it is desirable to detect the presence of flaws as soon as possible so corrective steps can be taken to eliminate the source of the flaws.

Prior patents disclose procedures for detecting the presence of flaws before a product cools. One such U.S. Pat. No. 4,024,470 to Vild et al entitled "Eddy Current Detector for Hot Test Pieces Having Cooling Fluid and Purge Features" discloses apparatus where a combination of a heat shield and a fluid coolant protects detectors from the heat of a hot workpiece.

The Vild et al and a number of other prior patents relating to eddy current testing are assigned to the Republic Steel Corporation, assignee of the present invention. Republic Steel patents which disclose control circuitry and apparatus to classify and mark the position of defects in steel bars are U.S. Pat. Nos. 3,108,230 to Judd et al and 3,263,809 to Mandula et al as well as the '470 patent to Vild et al. An improvement to the marking process of these patents is disclosed in recently issued U.S. Pat. No. 4,365,198 to Toth. U.S. Pat. No. 4,355,281 to Toth et al also concerns an eddy current test arrangement having two detection coils spaced along a workpiece path so that as the workpiece is rotated and translated past the coils flaws are detected. The disclosures of these five patents is incorporated herein by reference.

In a typical eddy current tester, an excitation coil is placed in proximity to a steel object under test. The coil is energized with an electric signal which creates magnetic fields which in turn create eddy currents in the steel. A flaw in the steel disrupts the eddy current flow and this disruption can be sensed by monitoring the induced current in a test coil. A prior art eddy current tester for relatively deep flaws includes both an excitation or energization coil to set up the eddy currents in the workpiece and a separate detector coil which is used in monitoring eddy currents.

Proposals have been made to modify the functioning of these prior eddy current testers. These proposals concern strengthening or enhancing a magnetic field in various locations in relation to a product under test. This enhanced magnetic field produces a stronger response in the test equipment monitoring the eddy currents The prior proposals include either a shield to selectively transmit a magnetic field to the surface of the product or, in the alternative, a rotatable magnetic field producing element moved in relation to the product. U.S. Pat. Nos. 3,152,302 to Allen et al and 4,203,069 to Davis depict these two proposals. These proposals, while recognizing a desirable effect, i.e. the selective enhancement of the response produced by the excitation coil, are believed to be ineffective in producing this result.

DISCLOSURE OF THE INVENTION

An improved eddy current tester is disclosed for detecting flaws in a workpiece. Flaws extending along an elongated workpiece are detected with enhanced reliability while the product is still very hot. Production of scrap product is thereby minimized.

The disclosed electromagnetic flaw detection system is adapted for detecting defects in metallic workpieces having generally cylindrical outer surfaces. The system includes a drive mechanism for propelling the workpiece along a path and excitation circuitry for producing a time varying electromagnetic field that induces a flow of eddy currents in the workpiece.

A generally cylindrical shield is provided which defines at least two indentations which are preferably in the form of apertures and which are longitudinally spaced along the path. The shield is mounted for rotation coaxially with the workpiece. The positioning of the shield is such that the aperture rotates about the workpiece within the varying electromagnetic field. Detection circuitry responds to the variations and eddy current flow to provide an indication of flaw locations along the workpiece surface.

The two longitudinally spaced rotating slots selectively disrupt the magnetic field at continuously changing locations about the workpiece and produce a signal output having an enhanced signal to noise ratio. The detection circuitry can distinguish between flaws extending longitudinally between the two apertures and flaws of a shorter length which do not extend between the apertures.

A preferred configuration of the apertures is of slots which extend generally parallel to the shield axis of rotation. The slots each have a width of approximately ⅛ inch and length of approximately 1 inch. These slots are offset at different angular orientations so that when a first aperture reaches a particular axial position, the second aperture trails behind by a well defined angular amount. This angular offset allows a preferred detection circuit to provide a readily observable output even for shallow workpiece flaws.

The combination of angularly offset slots and a differentially wound detection coils enhances the flaw detection capability. If an elongated flaw extends between the two slots in the rotatable sleeve, this flaw first produces a positive spike or pulse in a first detection coil and at a later time corresponding to the time it takes the slotted sleeve to rotate the second slot past the flaw, a negative going pulse is produced. In combination these positive and negative going pulses produce a large voltage spike which is easily sensed by the detection circuit.

The cylindrical workpiece is supported in its movement through the slotted sleeve so that it remains approximately centered within the sleeve. In a preferred embodiment this is accomplished with centering rolls on an exit side of a workpiece inspection station.

A preferred test assembly utilizes an air powered motor for rotating the slotted sleeve. The rotation of the sleeve is monitored and coordinated with an indicator such as an oscilloscope or strip recorder so that the occurrence of flaws can be visually observed.

From the above it should be appreciated that one object of the invention is an improved flaw detection system and method of flaw inspection for monitoring an elongated workpiece. This and other objects, advantages and features of the invention will become better understood when a detailed description of a preferred embodiment of the invention is described in conjunction with the accompanying drawings.

BEST MODE FOR CARRYING OUT THE INVENTION

Figure 1:
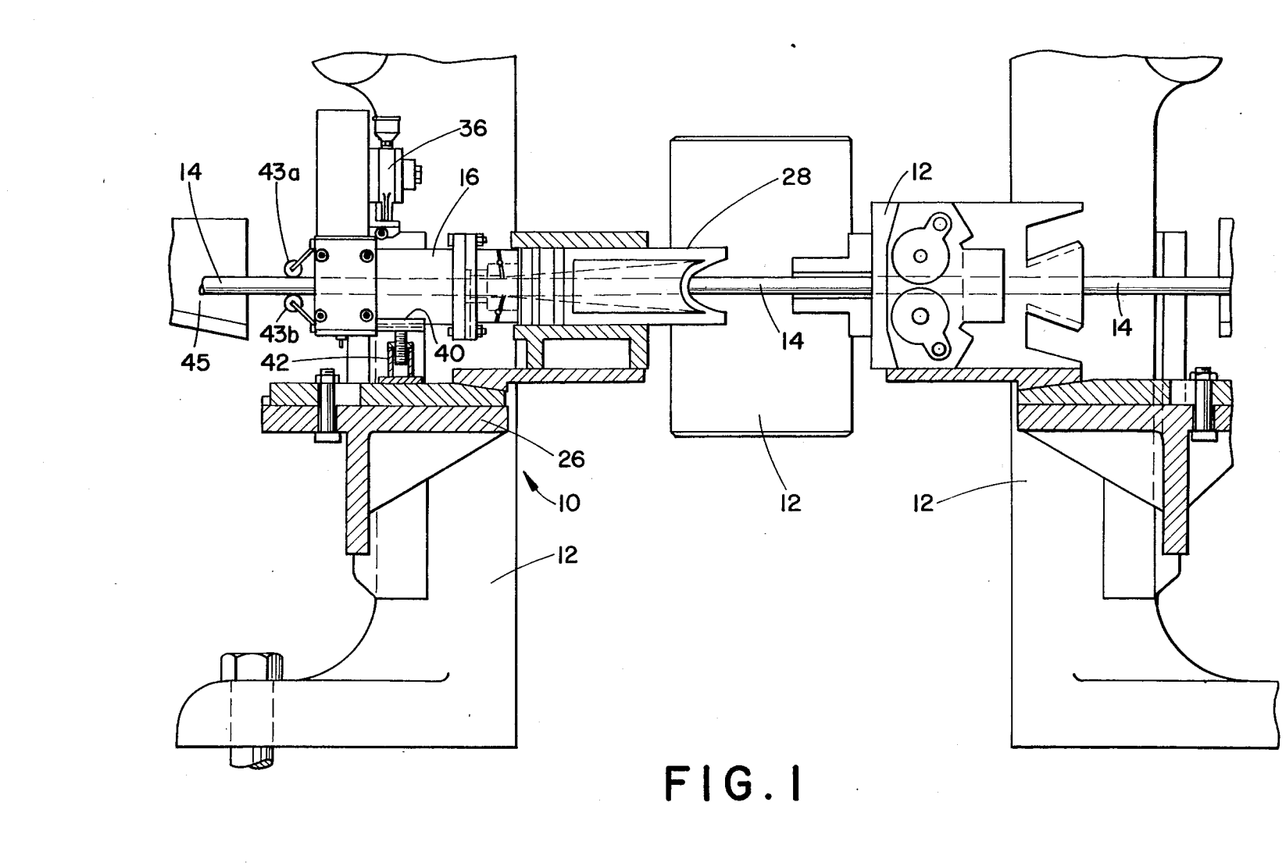
FIG. 1 is a side elevation view of a elongated workpiece test station.

Turning now to the drawings, and in particular FIG. 1, there is illustrated a workpiece shaping station 10 including a roll stand 12 for shaping a workpiece 14 as the workpiece moves along a path of travel to a test head 16. The workpiece 14 defines a generally cylindrical outer surface such as the outer surface of a bar or pipe. An entrance guide 28 also supported on the stand 12 directs the workpiece 14 through the test head 16. The temperature of the workpiece may be at room temperature or alternately, can be at an elevated temperature needed to shape the workpiece into its cylindrical cross-section. In the illustrated embodiment of the invention, the station 10 is adapted to inspect workpieces having an elevated temperature after they have been shaped by other apparatus upstream from the test head 16.

Figure 2:
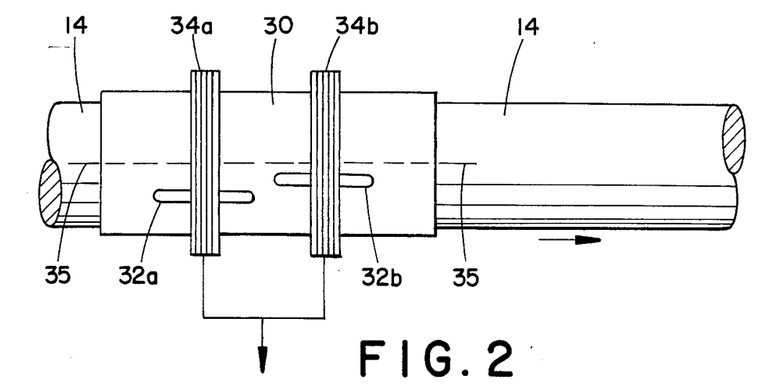
FIG. 2 is a schematic view of the elongated workpiece as it is moved through a rotatable slotted sleeve that selectively disrupts an eddy current field in the vicinity of the workpiece.
Figure 3:
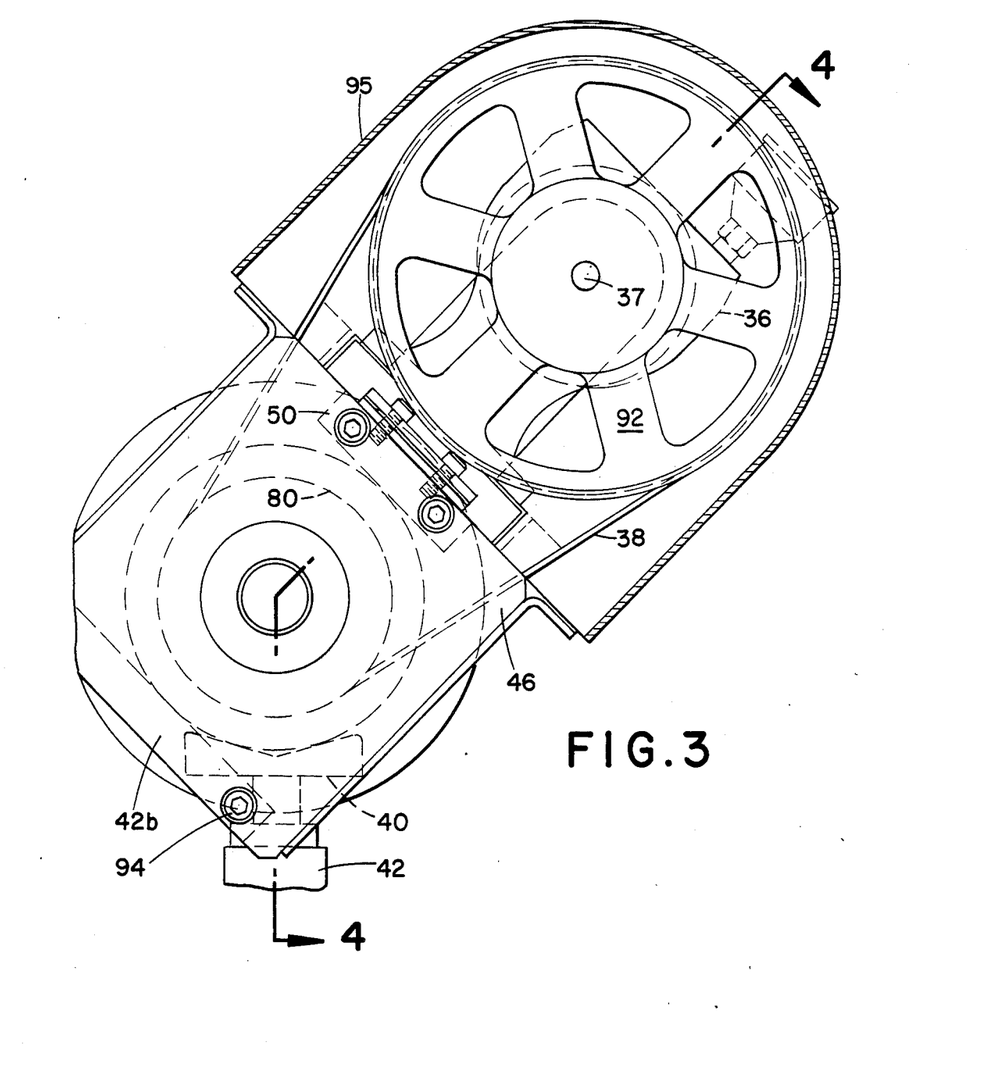
FIG. 3 is an end elevation view of part of the FIG. 1 test station showing a motor for rotating the sleeve.

FIG. 2 schematically illustrates certain components mounted within the test head 16. The head rotatably supports a cylindrical stainless steel sleeve 30 (FIG. 2) having elongated slots 32a, 32b along its length. The sleeve 30 is encircled by eddy current inducing coils 34a, 34b.

The encircling coils are positioned in relation to the slots 32 so that the coils 34 and the slots 32 are intersected by a common plane. During scanning of the workpiece 14, time varying energization signals are coupled to the coils 34 to induce eddy currents at the workpiece surface. The sleeve 30 and slots 32 are rotated to periodically disrupt the eddy current field and produce the electrical response the coils 34 exhibit in response to the passing of a workpiece flaw 35 beneath the coils 34. As an alternate to the slots 32, a series of parallel very narrow slits of the same length as the slots can be used to disrupt the field.

A motor 36 (FIG. 4) driven by a compressed air source (not shown) has an output shaft 37 that rotates the sleeve 30 through a drive belt 38. The motor 36 and test head 16 are both supported by a cradle 40 coupled to the stand 26 by a support jack 42. The jack raises and lowers the cradle 40 to accommodate the test heads 16. On an exit side of the test head 16, pinch rolls 43a, 43b (FIG. 6) support the workpiece 14 and center it within the sleeve 30 as it passes to an exit trough 45.

The rotatable sleeve 30 and coils 34 are positioned inside the test head 16 which is bounded at an entrance side by a tapered entrance guide 44 (FIG. 4) and at an output side by an end cap 46. The test head 16 is seen to be constructed of two metal enclosures in the form of an annular cup and an end cap 48, 50 coupled together by threaded connectors 52.

Figure 5:
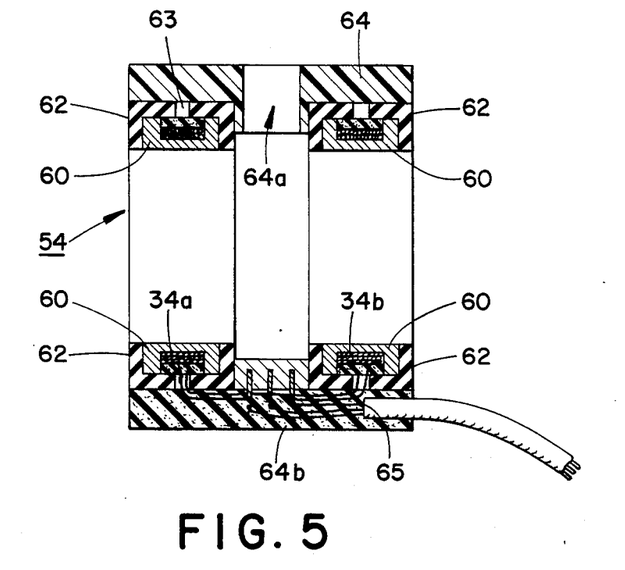
FIG. 5 is an enlarged sectional view of a test probe having diferentially coupled test coils.

FIG. 5 is an enlarged sectional view of a probe assembly 54 which is supported within the test head 16. The assembly 54 includes two bobbins 60 for supporting two coils 34a, 34b respectively. Two ferrite or powdered iron cores 62 respectively surround the bobbins and each defines a passageway 63 for routing conductors 65 that energize the associated coil. The cores 62 in turn are surrounded by and abut a plexiglass housing 64. The housing 64 defines a through passage 64a to allow water to be directed to the sleeve 30 for cooling. The housing 64 also defines a slot 64b to route the conductors 65 to the coils 34. A potting compound fills the slot 64b and passageways 63 to effect a fluid tight seal around the conductors.

Figure 4:
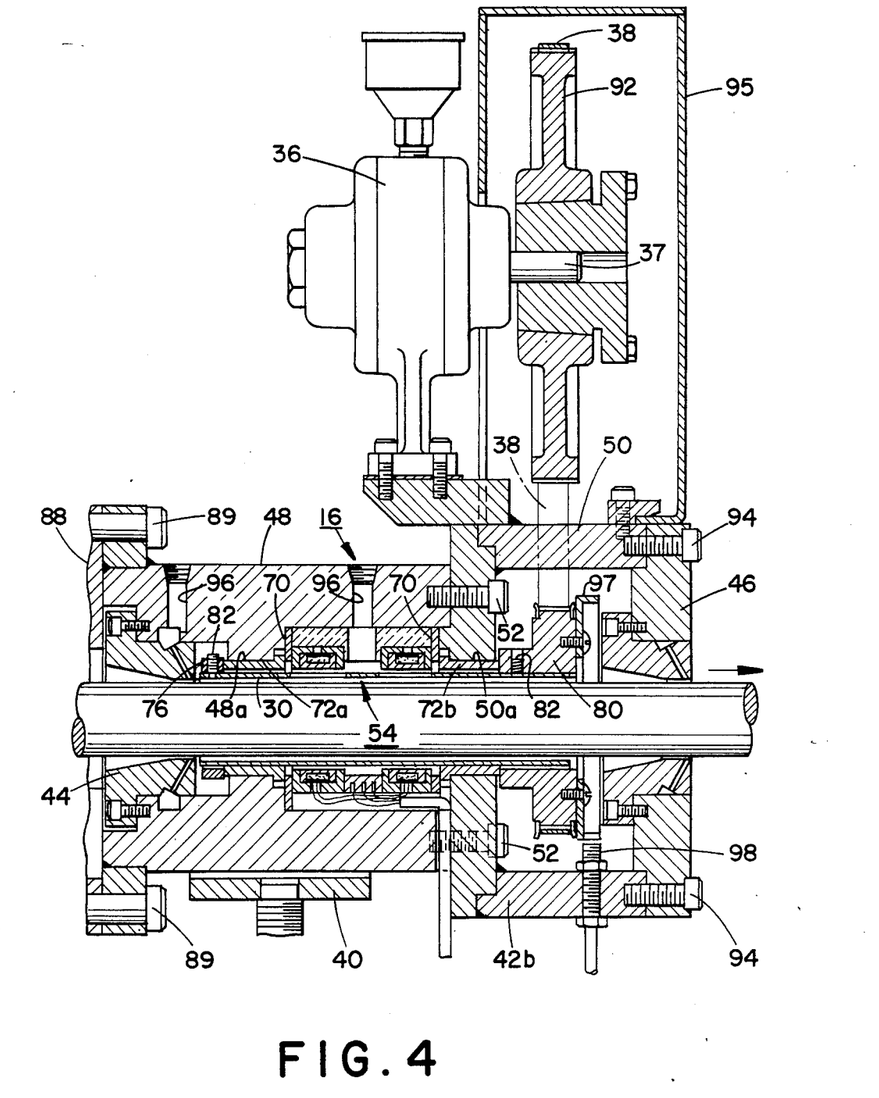
FIG. 4 is a view taken along the line 4—4 in FIG. 3.

The entire probe assembly 54 is supported inside the test head segment 48 and located axially by compressed rubber washers 70 (FIG. 4). The probe assembly 54 includes an axially aligned and spaced pair of cylindrical water lubricated thrust and journal bearings 72 that support the sleeve 30 for rotation. The bearings 72 are respectively positioned in two regions 48a, 50a of reduced diameter in the enclosures 48, 50.

The sleeve 30 is journalled in the bearings 72 within the enclosures 48, 50 and located axially in relation to the probe 54 by a collar 76 at one end of the probe assembly 54 and by a sprocket 80 at the other end. The collar 76 and a sprocket 80 are held in place by set screws 82.

The compressed washers 70 act against the bearings 72 to urge them into thrust absorbing relationship with the sleeve and sprocket respectively. To accommodate this thrust relationship and thermally induced expansion one or both of flanges 72a, 72b of the bearings will be spaced slightly from adjacent surfaces of the enclosures. These spaces, due to their small size, are not shown in the drawings.

The tapered entrance guide 44 is connected to the enclosure 48 by suitable connectors 86. The entire test head 16 mounted to the input guide 28 by coupling the test head 16 to an input guide mounting flange 88 with connectors 89 (see FIGS. 1 and 4).

The motor output shaft 37 is coupled to a drive sprocket 92 having teeth for engaging the belt 38 that engages the driven sprocket 80. With the driving belt properly in place, the end plate 46 is secured to the enclosure 50 with suitable connectors 94. A guard 95 is secured over the belt 38 and drive sprocket 92.

When testing hot workpieces for elongated flaws and the like, the probe assembly 54 and sleeve 30 are cooled by water introduced through two water inlets 96 shown in FIG. 4. The introduction of water to the vicinity of the test assembly 54 not only cools the sleeve 30 but lubricates the bearings 72 as well.

Control over the speed of rotation of the sleeve 30 is not necessary to correlate output signals from the coils with flaws extending along the workpiece. Coupled to the driven sprocket 80 is a timing event disk 97 having a metallic object that rotates with the disk and which is periodically sensed by an electromagnetic sensor 98. The output from the sensor 98 is used to synchronize an oscilloscope sweep rate with sleeve rotation.

Figure 6:
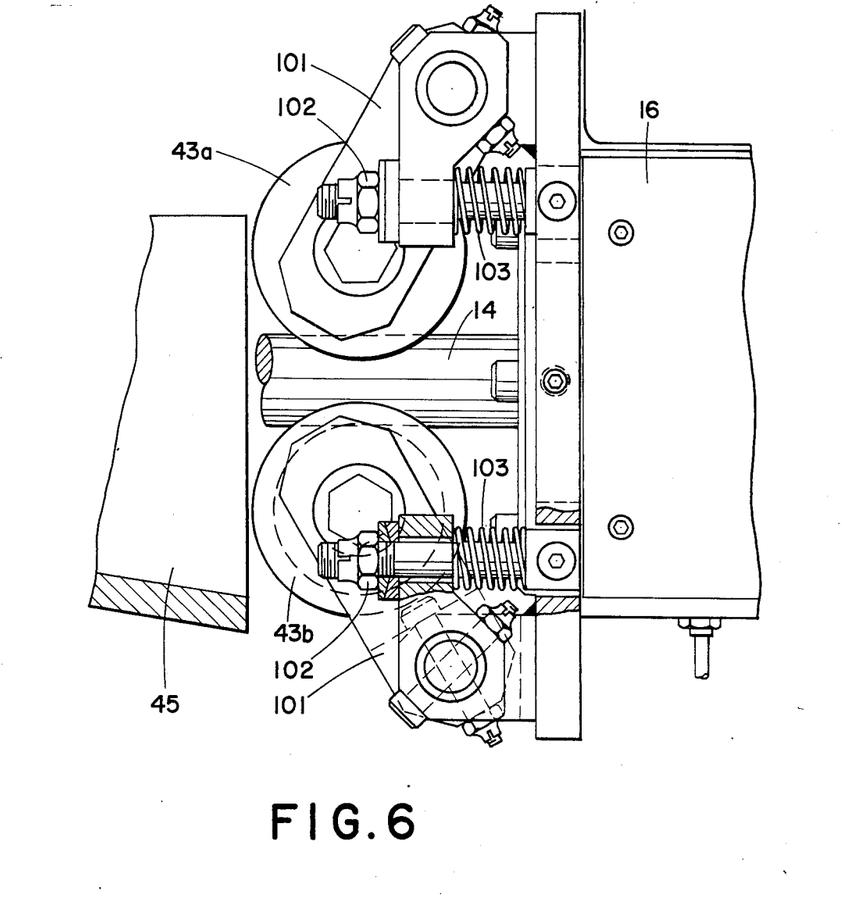
FIG. 6 is an elevation view of exit rolls for centering the workpiece within the slotted sleeve.

FIG. 6 shows details of the exit rolls 43a, 43b and the mounting of these rolls adjacent the test head 16. Each roller is mounted for rotation on an arm 101 attached to the test head 16. The positioning of each arm 101 in relation to the workpiece path can be adjusted by turning an adjusting nut 102 that pivots the arm. Compression springs 103 respectively bias the arms against the adjusting nuts 102 to fix the arm positions and thus the size workpiece the pinch rolls can accommodate and center.

Figure 7:
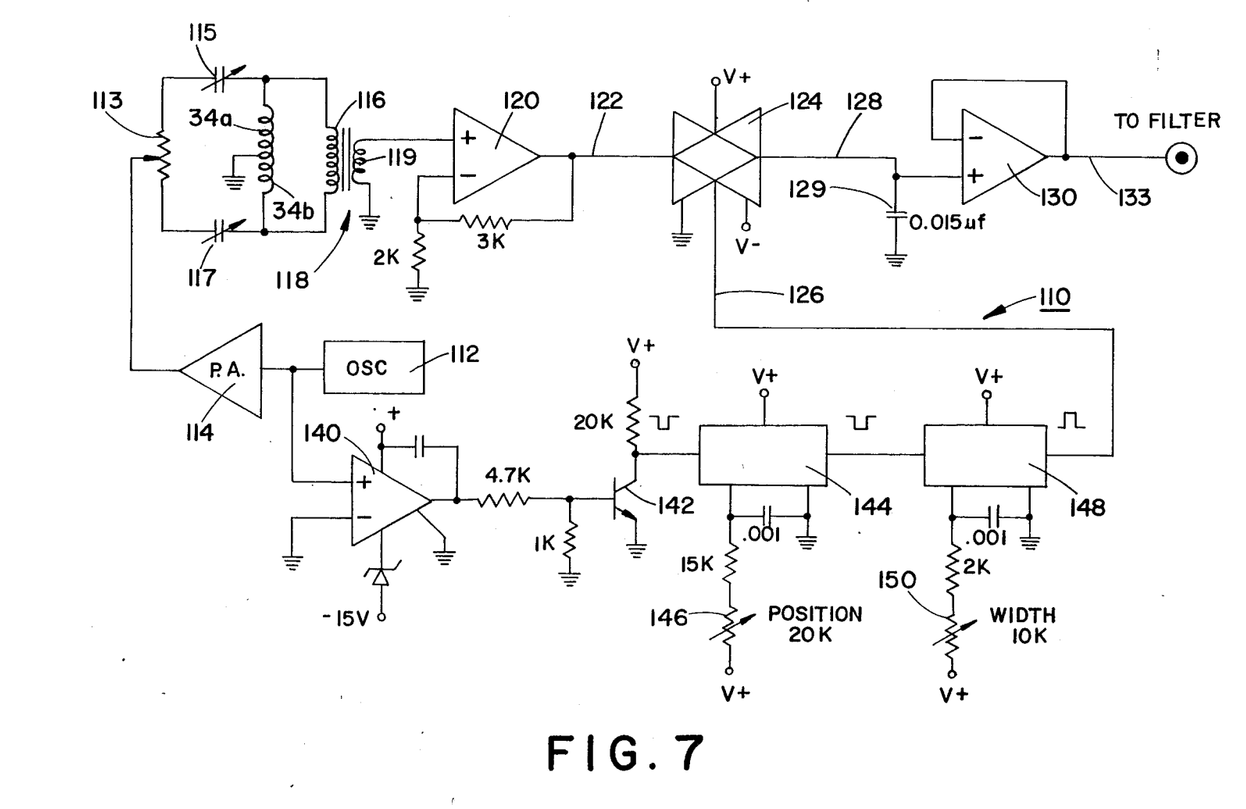
FIG. 7 is an electrical schematic of coil energization and flaw detection circuitry.

Turning now to FIG. 7, an energization and detection circuit 110 for the test coils 34 is illustrated. The circuit 110 both energizes and demodulates output signals from two test coils 34a, 34b. An oscillator 112 drives a power amplifier 114 which in turn is coupled to the two differentially wound coils 34a, 34b. Interposed between the power amplifier 114 and coils are a variable resistor 113 and two tuning and phase shifting variable capacitors 115, 117. These components allow the relative magnitude and phase of the alternating signals across the coils 34a, 34b to be adjusted to enhance sensitivity of the flaw sensing. The oscillator frequency 112 is adjustable and in a preferred embodiment is adjusted to produce a sinusoidal output having a frequency of approximately 40 kilohertz. This energization of the two coils 34a, 34b sets up magnetic fields which induce eddy currents at the surface of the workpiece 14.

Figure 9:
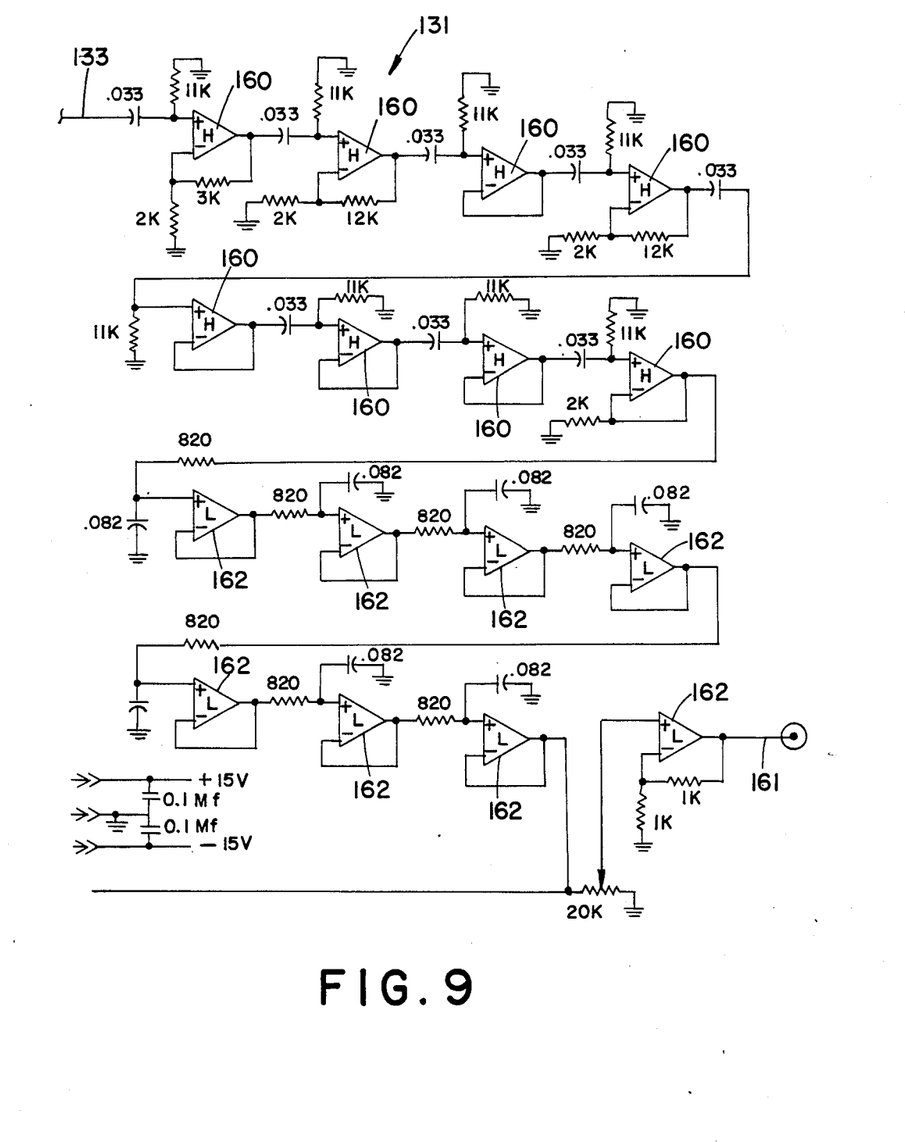
FIG. 9 shows a filter circuit for filtering out extraneous signals from analysis.

When these eddy currents are disrupted by the presence of a flaw, the self induced current through the coils is also disrupted. The interaction of the fields of the coil sleeve, and workpiece results in a spike or a pulse output from the coils 34a, 34b which is sensed by a primary 116 of a transformer 118. The output from a secondary 119 of the transformer 118 is coupled to an amplifier 120 having an output 122 coupled to an analog switch 124. The analog switch 124 has a gate input 126 which selectively transmits signals from the input 122 through the switch to an output 128 which is stored by a capacitor 129 and buffered by an amplifier 130. An output 133 from this buffer 130 is transmitted to a filter circuit 131 (FIG. 9) and then to circuitry which analyzes the flaws severity.

Figure 10:
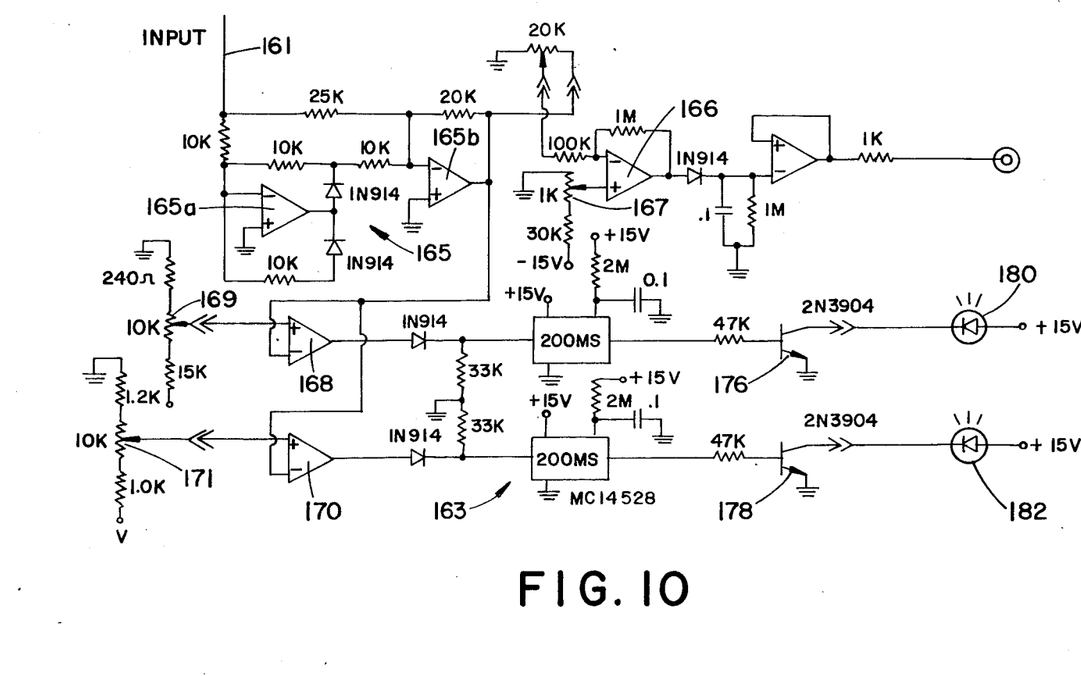
FIG. 10 is a schematic of circuitry for analyzing an output from the FIG. 9 filter circuit.

One system for analyzing the severity of the defects is disclosed in U.S. Pat. No. 4,365,198 to Toth entitled "Method and Apparatus For Detecting, Classifying, and Marking Defects in a Workpiece with Improved Timing Control" which issued Dec. 21, 1982 and is incorporated herein by reference. An additional circuit is illustrated in FIG. 10.

A gate signal for the analog switch gate input 126 also originates at the oscillator 112. The gate signal is a pulse which periodically couples the analog gate input 122 to its output 128. An output from the oscillator 112 is coupled to a comparator 140 which transmits a positive portion of the alternating current signal from the oscillator 112 to a switching transistor 142 for converting the analog output from the oscillator 112 into a series of pulses. A first one shot 144 produces a delay in these pulses of from 7 to 16 microseconds depending on the setting of a variable 20k resistor 146. A second one shot 148 varies the width of its output pulse from one to five microseconds depending on the setting of a 10k variable resistor 150.

A 40 kilohertz oscillator output produces a time or period between peak-to-peak signals of 25 microseconds. The ability to shift and shape the gating signal within this 25 microsecond period allows the user to maximize the output 128 and therefore the sensitivity of the flaw detection.

Figure 8:
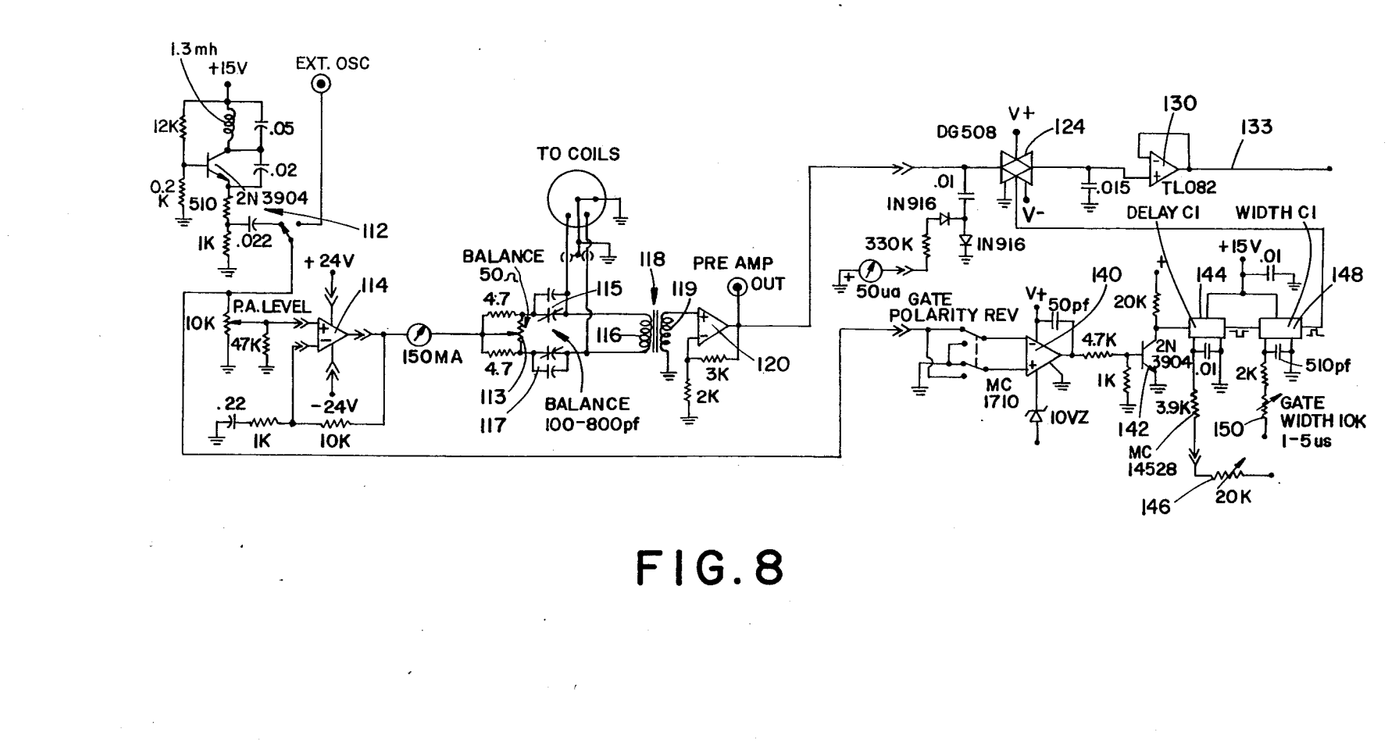
FIG. 8 is a more detailed schematic of the FIG. 7 circuitry.

A more detailed schematic of this circuitry 110 is presented in FIG. 8. Like reference numerals have been used for components in the two schematics.

The filter circuit 131 (FIG. 9) comprises four integrated circuits, each having four operational amplifiers for a total of sixteen operational amplifiers. The filter circuit 131 is divided into a high pass filter and a low pass filter with the first eight operational amplifiers 160 making up the high pass filter and the next eight operational amplifiers 162 making up the low pass filter. In a preferred embodiment of the invention, these filters in combination attenuate all signals having frequencies less than or greater than approximately one kilohertz. In this way extraneous signals in the noisy environment of a steel production facility are eliminated and only signals generated by flaws in the workpiece 14 will be transmitted to an output 161 to a detection and classifying circuit 163.

The circuit 163 (FIG. 10) takes an output signal from the filter 131, rectifies it and transmits it to a number of comparators which classify the defects as to severity and depth. A detailed schematic for this circuitry is presented in FIG. 10. Briefly, the output from the filter is coupled to a precision rectifier 165 having two operational amplifiers 165a, 165b and transmitted to three comparator amplifiers 166, 168, 170. A refernce input on each of these comparators can be adjusted using variable potentiometers 167, 169, 171 coupled to these reference inputs. Based upon the magnitude of the output from the filter circuit 131, the comparators 166, 168, 170 either produce a low or high output.

In a preferred embodiment of the invention, an output 174 from the amplifier 166 is coupled to a recorder for generating a permanent record of the output from the coils. The output from the comparators 168, 170 selectively turns on two transistors 176, 178 which in turn activate two visual indicators 180, 182. In combination a first comparator 168 and indicator 180 act as a shallow seam or flaw detector and a second comparator 170 and indicator 182 act as a deep seam or flaw detector. It should be appreciated that an audible alarm can also be generated based upon a comparison between the output from the coils 34 and a reference level.

In operation, the motor 36 drives the sleeve 30 causing it to rotate at a fixed rate of about 100 hertz about the workpiece 14 as the workpiece moves through the test head. In the event a flaw 35 extends beneath one or the other of the coils 34a, 34b, the magnetic field will be disrupted and an output from the transformer 118 generated. The slots 32 pass over the flaw 35 at different times and due to the differential winding of the coils 34a, 34b, a positive and then a negative going spike is produced by the transformer if the flaw extends beneath both coils 34a, 34b. These positive and negative signals in combination generate a sharp spike from the transformer 118 at the frequency of rotation of the sleeve 30 that is easily detectable by the analyzing circuitry of FIG. 10. Without the angular offset between the two slotted portions of the sleeve, the differential winding of the coils 34a, 34b, would result in a cancellation of the signals and even the severest of flaws would produce no output.

The preferred sleeve 30 is constructed of 1/16" stainless steel and the two slots extend completely through the sleeve with a width of ⅛ inch and a length of approximately 1 inch. Experimentation has indicated, that a similar effect is produceable, even though the slots do not extend entirely through the sleeve 30 but instead only form indentations in the sleeve. This advantageous discovery allows a sleeve 30 to be used without foreign matter from the region of the workpiece 14 passing through the slots 32 to the region of the coils 34a, 34b. If the slots 32 do extend completely through the sleeve 30 passage of foreign matter to the coils can be avoided by plugging the slots with nonconductive material. In an embodiment in which narrow slits rather than slots are formed in the sleeve 30 plugging of the slits is easily accomplished with the same non-conductive material.

It should be appreciated therefore that although the invention has been described with a degree of particularity, it is the intent that the invention include all modifications and/or alterations falling within the spirit or scope of the appended claims.

We claim:

1. An electromagnetic flaw detection system for detecting defects in metallic workpieces having generally cylindrical outer surfaces, said system comprising:
   (a) a drive means for propelling a workpiece along a workpiece travel path;
   (b) excitation circuitry mounted in proximity to said workpiece travel path for producing a time varying electromagnetic field along the path for inducing flow of eddy currents in said workpiece;
   (c) a generally cylindrical shield defining therein at least two indentations that disrupt a surface of said shield, longitudinally spaced along the length of said shield;
   (d) apparatus for rotatably mounting said shield substantially coaxial with said path at a longitudinal position along the path so that said indentations in said shield are rotatable within said varying electromagnetic field;
   (e) rotation means for rotating the cylindrical shield to cause the identations to pass through and disrupt the varying electromagnetic field; and
   (f) detection circuitry mounted in proximity to said workpiece travel path radially outside said shield for responding to variation in electromagnetic energy induced by eddy current flow in said workpiece to provide an indication of the severity of a workpiece flaw.

2. The system of claim 1, wherein said shield comprises electrically conductive material.

3. The system of claim 1, wherein said indentations extend through the sleeve to define slots whose longitudinal dimension extends generally parallel to the axis of said shield.

4. The system of claim 1, wherein said detection circuitry comprises two differentially wound detection coils and the indentations are located at different angular orientations about the shield circumference beneath said two differentially wound detection coils.

5. The system of claim 1, wherein said shield defines apertures as two slots whose length dimension extends generally parallel to the shield axis, and wherein said slots are both angularly and longitudinally displaced from one another with respect to the cylindrical shield.

6. The system of claim 1, wherein said shield comprises a portion of stainless steel material.

7. The system of claim 1, wherein the shield defines apertures each having a length of approximately 1 inch and a width of approximately ⅛ inches.

8. The system of claim 1, further comprising filtering circuitry for suppressing spurious signals which would, if not so suppressed, produce spurious flaw indicating signals in response to physical vibration of the shield while rotating.

9. The system of claim 4, wherein each of said differentially wound coils is connected to a ground connection and has a non-grounded end connected to a ground connection and has a non-grounded end connected to said exicitation circuitry, said coils being spaced along the workpiece travel path to overlap said indentations and produce output signals in response to flaws extending beneath both coils.

10. The system of claim 1, wherein said excitation circuitry comprises circuitry for producing said varying electromagnetic field at a plurality of frequencies.

11. An electromagntic flaw detection system for detecting defects in metallic workpieces having generally cylindrical outer surface, said system comprising:

(a) excitation and detection circuitry mounted in proximity to a workpiece travel path for producing an alternating current time varying electromagnetic field for inducing eddy current flow in a workpiece moving along a travel path; said circuitry also responding to variation in electromagnetic energy induced by eddy current flow in said workpiece to provide an indication of a workoiece defect, said circuitry comprising two differentially wound coils coaxial with and surrounding the travel path at spaced locations along said travel path;

(b) a generally cylindrical shield having two angularly offset indentations longitudinally spaced along the length of the shield;

(c) means for mounting said shield substantially coaxially with the path such that the shield and thw workpiece are relatively rotatable and said indentations are located radially within said detection coils;

(d) means for rotating the shield with respect to said workpeice;

(e) a drive means for relatively moving the two coils and said workpiece along the travel path; and (f) analysis means, electrically coupled to said excitation and detection circuitry to analyze signal outputs from the differentially wound coils to sense defects having a length extending beneath both indentations.

12. The apparatus of claim 11 additionally comprising means to center said workpiece concentrically within said shield as it moves along said path.

13. A method for detecting defects in metallic workpieces having generally cylindrical outer surfaces, said method comprising the steps of:

(a) propelling a workpiece axially along a path;

(b) inducting eddy current flow in the workpiece with a time varying electromagnetic field as the workpiece moves along the path;

(c) rotating a cylindrical shield coaxially with respect to the workpiece, said shield having two indentations that are longitudinally spaced and angularly offset from each other to disrupt the eddy currents in two longitudinally separate locations that circumferentially move about the workpiece surface; and (d) detecting variatons in electromagnetic radiation induced by eddy current flow in the workpiece at said two separate locations indicative of a workpiece defect extending between said longitudinally separate locations.

14. The method of claim 13 where the detecting step is accomplished with two differentially wound sensing coils to produce opposite polarity signals when the longitudinally separate locations encounter an elongated flaw.

15. The method of claim 13, further comprising the step of suppressing spurious signals which would, if not so suppressed, produce spurious flaw indicating signals in response to physical vibration of the shield while rotating.

16. An eddy current type flaw inspection system comprising:

(a) a flaw inspection mechanism including excitation and detection coil structure;

(b) means for establishing a path of relative travel between the inspection mechanism and a worlpiece being inspected;

(c) the inspection mechanism including a tubular conductive element around the path and between at least an excitation portion of the coil structure and the workpiece;

(d) the element including first and second indentations spaced from one another longitudinally of the path;

(e) a drive operably connected to the tubular conductive element and the means for establishing a path of relative travel to effect relative rotation of the element and a workpiece as such workpiece is inspected; and (f) monitoring circuitry connected to said excitation and detection coil structure to monitor eddy current induced electromagnetic signals caused by the field modifications resulting from rotation of said indentations through the field created by said excitation and detection coil structure.

17. The flaw inspection system of claim 16 wherein the monitoring circuitry comprises a filter circuit that selectively transmits signals from the excitation and detection coil structure of a specified frequency range.

18. The flaw inspection system of claim 16 where the flaw inspection mechanism excitation and detection coil structure comprises two coils differentially wound and spaced along the path of relative travel with each coil overlapping at least a portion of one of said first and second indentations and wherein said indentations are angularly offset about the circumference of said tubular conductive element.

19. The flaw inspection system of claim 18 where the flaw inspection mechanism comprises:

(a) energizing means coupled to said two coils to excite said coils at a desired frequency; and (b) gating circuitry coupled to the energizing means to coordinate passage of the eddy current signals to the monitoring circuitry and thereby enhance the sensitivity of the inspection system.

20. The flaw inspection system of claim 18 wherein the indentations extend completely through the tubular conductive element to form apertures therein.

* * * * *